(12) United States Patent
Hurwitz

(10) Patent No.: US 7,498,072 B2
(45) Date of Patent: *Mar. 3, 2009

(54) LONG SERVICE LIFE SCENT DISPERSING MAT APPARATUS

(76) Inventor: Marni Markell Hurwitz, 81 Mosle Rd., Far Hills, NJ (US) 07931

( * ) Notice: Subject to any disclaimer, the term of this patent is extended or adjusted under 35 U.S.C. 154(b) by 846 days.

This patent is subject to a terminal disclaimer.

(21) Appl. No.: 11/007,725

(22) Filed: Dec. 8, 2004

(65) Prior Publication Data

US 2005/0106077 A1  May 19, 2005

Related U.S. Application Data

(63) Continuation-in-part of application No. 10/712,343, filed on Nov. 14, 2003, now Pat. No. 6,991,842.

(51) Int. Cl.
*B23B 3/10* (2006.01)
(52) U.S. Cl. .......................... 428/71; 428/68; 422/120; 422/123; 15/215
(58) Field of Classification Search ............... 422/120, 422/124, 123; 428/68, 71, 905; 15/215
See application file for complete search history.

(56) References Cited

U.S. PATENT DOCUMENTS

| | | | |
|---|---|---|---|
| 3,993,444 A | 11/1976 | Brown | 21/126 |
| 4,161,284 A * | 7/1979 | Rattan | 239/43 |
| 4,346,059 A | 8/1982 | Spector | 422/125 |
| 4,695,434 A | 9/1987 | Spector | 422/116 |
| 4,876,135 A | 10/1989 | McIntosh | 428/74 |
| 5,209,784 A * | 5/1993 | Bellman | 134/25.4 |
| 5,565,148 A | 10/1996 | Pendergrass, Jr. | 261/30 |
| 5,651,942 A | 7/1997 | Christensen | 422/125 |
| 5,744,209 A | 4/1998 | Parkes | 428/96 |
| 6,031,967 A | 2/2000 | Flashinski et al. | 392/390 |
| 6,154,607 A | 11/2000 | Flashinski et al. | 392/390 |
| 6,173,675 B1 | 1/2001 | Licciardo | 119/28.5 |
| 6,254,836 B1 * | 7/2001 | Fry | 422/124 |
| 6,309,986 B1 | 10/2001 | Flashinski et al. | 442/125 |
| 6,361,752 B1 | 3/2002 | Demarest | 422/306 |
| 6,551,560 B1 | 4/2003 | Flashinski et al. | 422/125 |
| 6,581,915 B2 | 6/2003 | Bartsch et al. | 261/26 |
| 6,722,578 B2 | 4/2004 | Skalitzky et al. | 239/57 |
| 6,991,842 B2 * | 1/2006 | Hurwitz | 428/71 |

* cited by examiner

*Primary Examiner*—Sean E Conley
(74) *Attorney, Agent, or Firm*—Ernest D. Buff & Associates, LLC; Ernest D. Buff; Dave Narasimhan

(57) ABSTRACT

A long life scent dispersing mat apparatus uses an outer housing with apertures appointed to disperse a scent or fragrance. The fragrance is provided in a fragrant body which is a springy spongy rubber or polymeric sponge soaked with essential oils that have high vapor pressure at ambient temperatures. The fragrant body is inserted into an inner pouch which has small apertures and the stagnant air within the inner pouch attains saturation of fragrance vapor, thereby stopping further evaporation of the essential oils. When the scent-dispersing mat is stepped on, the inner pouch releases the saturated fragrant vapor into the interior of the outer housing and it is released to room air through apertures provided in the outer housing. When force on the mat is released, the fragrant body recovers its original shape and the inner pouch draws fresh make up air and essential oils volatilize until saturation is reached.

20 Claims, 4 Drawing Sheets

LONG SERVICE LIFE SCENT DISPERSING MAT APPARATUS

This is a Continuation-In-Part of application Ser. No. 10/712,343, filed Nov. 14, 2003 now U.S. Pat. No. 6,991,842 B2 for "Scent Dispersing Mat Apparatus", the disclosure of which is hereby incorporated in its entirety by reference thereto.

BACKGROUND OF THE INVENTION

1. Field of the Invention

The present invention relates to a mat apparatus for dispersing scent; and more particularly to an apparatus capable of housing a scented insert for dispersion of scent when the apparatus receives a force or is compressed.

2. Description of the Prior Art

Many patents address issues related to the dispersion of scent into a room, and in particular to the dispersion of scent by way of a scent dispersing apparatus in the form of a mat. The volatile fragrant oils in most of these patents require a heating element to evaporate the fragrance. In many cases, a blower is needed to disperse the scent into the room.

U.S. Pat. No. 3,993,444 to Brown discloses an intermittent time controlled vapor-dispensing device. This device has an open top container holding a quantity of a volatile paste-like material within the interior of the container, which material is intermittently dispensed in vapor form to the ambient atmosphere. An electric circuit controlled motor is intermittently energized at predetermined time intervals to rotate a fan in the device for specific time periods to direct currents of air onto the exposed surface of the paste. This transforms the paste into vapor that is discharged outwardly from the container. A portion of the device is defined by apertured walls that surround the container, with the apertures of sufficiently small size so that the container in the device is substantially concealed. The apertures serve the functions including permitting air to flow into the interior of the device through a first portion, and discharging vapors through a second portion of the apertures. As the fan operates the vapor from the paste material configures into a number of small streams and discharges outwardly through the second portion of the apertures and disperses into the ambient atmosphere. In order to vaporize and disperse the paste, an electrical current is passed through a heater and the fan must be driven. The vapor-dispensing device disclosed by the patent is not a mat. Furthermore, the dispensing device requires electrical connection for heating and driving a fan in order to facilitate the vaporization, streaming and dispersion of the scent particuli.

U.S. Pat. No. 4,346,059 to Spector discloses an aroma-generating lamp structure in which a pad of porous material impregnated with an aroma-producing liquid is disposed under a vent in a substantially enclosed housing. An electrical heating element placed in the housing acts to heat and expand the air confined therein to create a positive air pressure producing a pressure differential between the heated air and the atmosphere above the vent. As a consequence of which the heated air is driven through the pad to rapidly volatilize the liquid and exude an aromatic vapor through the vent into the atmosphere. This aroma-generating lamp is not a mat and relies on lamp heat to drive the aroma into the atmosphere.

U.S. Pat. No. 4,695,434 to Spector discloses an aroma-generating unit. The aroma-generating unit is adapted to periodically discharge bursts of aromatic vapor into the atmosphere, with non-aromatic intervals between the bursts. These non-aromatic intervals have duration sufficient to avoid desensitizing the olfactory response of those exposed to the unit. The unit includes a hollow case whose upper wall has a vent therein and whose sidewall has a slot to receive a replaceable cartridge provided with a porous mat impregnated with an aromatic liquid. When fully inserted, the cartridge is disposed below the vent and serves to define an air-confined chamber within the case. Disposed in this chamber is an electrical heater that is periodically energized by power pulses to heat and expand the confined air and to produce a positive pressure in the chamber forcing the heated air through the impregnated mat to rapidly volatilize the liquid. Bursts of aroma are produced and discharged into the atmosphere through the vent, and are separated by relatively long, non-aromatic intervals. The disclosed aroma-generating unit is not a mat and utilizes electrical heat to produce a positive pressure of the aroma vapor.

U.S. Pat. No. 4,876,135 to McIntosh discloses a floor mat with disposable absorbent pad. The automobile floor mat comprises a jacket member having a throat opening in a free edge for receiving an insert sheet of absorbent material, such as cardboard. The top sheet of the jacket has openings for the passage of foreign matter, including spilled liquids. The insert sheet is disposed under the top sheet and retains foreign matter disposed thereon through the openings in the top sheet. The back surface of the insert is coated with a water resistant coating. After the insert sheet is soiled it can be removed and cleaned or replaced by a new sheet with the soiled sheet discarded. The insert sheet may be coated with a deodorizing liquid whereby to release a pleasant smelling scent especially when the floor mat is used in an automobile. The insert sheet is supposed to absorb liquids and to meet this functionality the cells in the sheet must be empty and therefore they cannot contain any significant reservoir of vaporizable scent. Furthermore, the automobile mat provided by the patent is not cushioned since the insert sheet is rigid.

U.S. Pat. No. 5,565,148 to Pendergrass, Jr. discloses a device for selectively providing a multiplicity of aromas. The device may deliver one or more aromas at selected times and include a housing with a receptacle and an aroma delivery device detachably received in the receptacle. A reservoir contains a volatile aroma material and a diffusion rate-controlling structure which at least partially covers the reservoir to provide controlled release of the aroma. The aroma delivery device includes a carrier having a plurality of aroma-bearing elements that are selectively communicated with an air passageway for providing one or more aromas as desired. The device is especially useful for providing a realistic sensory experience in an interactive or non-interactive use, and may be used in such diverse settings as the entertainment industry, the educational training field or a medical arena. This multiplicity aroma device is not a mat and requires opening of diffusion controlling structure to release selected aroma.

U.S. Pat. No. 5,651,942 to Christensen discloses an aromatic fragrance generator. The aromatic fragrances generator is provided for supplying aromatic fragrances to the atmosphere. The fragrance generator employs a heating element in a container to heat a fragrance base material contained in a receptacle to supply a pleasant aroma to the atmosphere, primarily to eliminate bathroom and kitchen odors. The disclosed fragrance generator does not involve a mat capable of releasing scent upon subjection to force. Rather, the disclosed generator utilizes a heating element and a fragrance base material that needs to be heated in order to release fragrance into the atmosphere.

U.S. Pat. No. 5,744,209 to Parkes discloses a scented mat product and method for making the mat product. The patent discloses a low cost, high quality, durable mat product having a fragrance or scent incorporated in the backing material thereof. The backing has a polyvinyl chloride based composition so that the scent is evenly dispersed throughout the environment of the mat for an extended period of time. Also disclosed is a method for making the mat product by adding a scent or fragrance to the backing material used in the mat product prior to securing the backing material to a textile layer. The disclosed mat provides that the scent is retained in the backing layer and is always evaporating. As a result of constant evaporation the mat inherently has a limited usable lifetime as the scent is virtually exhausted and therefore has a short duration as a scented mat product.

U.S. Pat. No. 6,173,675 to Licciardo discloses aromatherapy mats for pets. The mattress, mat or bed for animals comprises a soft and comfortable mat which-contains aromatherapy herbs having volatile components which aid and enhance certain behaviors in cats and dogs when laid upon. The mat is constructed with layers of soft fiber filling material and herbs are arranged between the layers and an outer cover of the mat. The scent and volatile effects of the herbs are able to emerge through the layers of the filling material and be inhaled by the pet to render the desired behavior. The mat relies on volatile components from the herb to evaporate through the porous soft fiber layer and the quantity of volatile aroma in herbs is inherently small. Moreover, constant evaporation provides a very limited time for aroma release.

U.S. Pat. Nos. 6,031,967, 6,154,607 and 6,309,986 to Flashinski, et al. disclose mats for dispensing volatile materials. The multi-layered mats are for dispensing volatile vapors such as insecticides. One layer is a carrier layer impregnated with the volatile. It is secured to at least one metal layer. The metal layer spreads the heat from a heater, thereby minimizing hot spots. Additional layers may be provided to provide a further heat distribution or temperature step down. An air gap can be provided between two of the layers. The disclosed mat is a heated device requiring heating in order to release volatile vapors. The volatile vapors are not released merely by the exertion of force upon the mat.

U.S. Pat. No. 6,361,752 to Demarest, et al. discloses an apparatus for volatilizing and dispensing a chemical into a room environment. An air quality modification apparatus for dispensing a volatile material, such as for scenting the air, controlling pests, allergen control, or the like, includes an electric motor having a rotor and a coil. When electric current is applied, the coil produces both heat and an electromagnetic field that causes rotation of the rotor. A source of the volatile material is located adjacent to the coil so as to be volatilized by the coil's heat. An impeller, attached to the rotor, moves air across the volatile material and blows the vapors away from the apparatus. Energy efficiency is provided by employing the electric motor coil as the source of heat to vaporize the volatile material. Also disclosed is a refill supply of a volatile material for use with such an air quality modification apparatus. This apparatus is not a mat and requires heating by passage of electrical current and a fan to drive the vapors into the atmosphere.

U.S. Pat. No. 6,551,560 to Flashinski, et al. discloses a two-stage dispensing mat. The two-stage mat is comprised of two materials varying either in thickness, thermal conductivity and/or porosity (and coated with like volatile material), or coated with volatile materials having different vaporization pressures. When the mat is heated, the two mats volatilize the fragrance at different rates providing for both an instant burst of volatile and then a sustained vaporization of volatile. Methods of using such mats are also disclosed. The disclosed mat requires heating to evaporate volatile fragrance from a two-stage mat which evaporates the fragrance at different rates.

U.S. Pat. No. 6,581,915 to Bartsch, et al. discloses a dispensing device for dispensing scents. The dispensing device dispenses scents into the environment and contains one or more scents or aromatic materials. The dispensing device includes housing and a removable, reusable/replayable, closed, multiple scent-containing article which is removably inserted into or onto the housing. The scent is released by unlocking a scent closure mechanism and once unlocked, it is constantly evaporating the fragrance. The disclosed dispensing device is not a mat and does not utilize the controlled release of scent through application of force upon a surface, but rather continuously dissipates scent once a closure mechanism is released.

U.S. Pat. No. 6,722,578 to Skalitzky, et al. discloses an apparatus for dispensing volatile materials. A dispenser with a lid laminate providing controlled release of a volatile material contained in a tray is disclosed. The lid includes a vapor impermeable, removable outer laminate and a vapor permeable inner layer covering an open side of the tray. The outer laminate includes layers of polyethylene terephthalate (PET) and aluminum foil removably adhered to the inner layer of biaxially oriented polypropylene (OPP) by an ethylene acrylic acid copolymer. Bottom and sidewalls of the tray are constructed of a metal/polymer pressure-formed colored tray laminate impermeable to the vapors and volatile material. The tray has a peripheral lip with an outer surface of cast polypropylene to which the vapor permeable inner layer of the lid is heat-sealed. The vapor of fragrance is released continuously once the barrier is removed. The apparatus disclosed is not a mat.

There remains a need in the art for a cushioned mat, which reliably dispenses scent when stepped on without continuously releasing the fragrance, thereby providing long service life for a mat that is used on household floors mat or land vehicles.

SUMMARY OF THE INVENTION

The present invention provides a scent-dispersing mat which has a flexible outer housing made from a rubber or polymeric material. The polymeric material for the outer housing may be chosen from polyethylene, polyvinyl chloride or other suitable polymeric material. The outer housing has an upper surface, lower surface and side surfaces. Apertures having a diameter ranging from 0.05 mm to 1 mm are provided on the upper and side surfaces to dispense scent. Preferably, the apertures are located only on the side surfaces since the apertures on the upper surface may be susceptible to becoming clogged with dirt and debris. The side surface of the outer housing has a resealable opening for inserting an inner pouch, which carries a fragrant body. This resealable opening may be in the form of a tongue and grove pressed or zipped closure.

The inner pouch is similar in structure to the outer housing but with smaller diameter apertures ranging in diameter from 0.01 mm to 0.4 mm and designed to contain the fragrant vapor evaporated by the fragrant body, which is inserted into the interior of the inner pouch. The fragrant body is a springy spongy rubber or polymeric member, which is soaked in essential oils that have high vapor pressure at ambient temperature. As a result, the stagnant air in the inner pouch is enriched by the fragrant vapor until it reaches equilibrium saturation and at this point, the essential oils in the fragrant body no longer evaporate fragrant vapor. The inner pouch also has a resealable opening to insert a fragrance body.

When the scent-dispersing mat is stepped on the outer housing is squeezed by this application of force and this in turn squeezes the inner pouch releasing the saturated vapor through the small apertures of the inner pouch into the interior of the outer housing. The scent exits the outer housing through the apertures provided, thus filling the room. When the force on the mat is released, the springy fragrant body recovers to its original shape, thereby expanding the inner pouch and drawing make up air into the interior of the inner pouch through the small apertures provided. At this stage the air in the inner pouch is no longer at saturation and the essential oils evaporate the fragrance until saturation. The apertures may be provided with outward opening flaps for dispersing the saturated vapor and inwardly opening flaps for entry of make up air. These flaps operate in only one direction and are closed when they are not in use.

The springiness of the fragrant body may be improved by attaching two rigid metallic or polymeric sheets interconnected to each other by a compression spring. This fragrant body assembly is inserted into the inner pouch and springs back to its original dimension when force is released.

The fragrant body is replaced when all the essential oils have been exhausted by evaporation. This is a very easy process and all one needs to do is open the resealable openings in the outer housing and inner pouch, insert a new fragrant body and close the resealable openings.

BRIEF DESCRIPTION OF THE DRAWING

The invention will be more fully understood and further advantages will become apparent when reference is had to the following detailed description of the preferred embodiments of the invention and the accompanying drawing, in which.

DETAILED DESCRIPTION OF THE INVENTION

Figure 1:
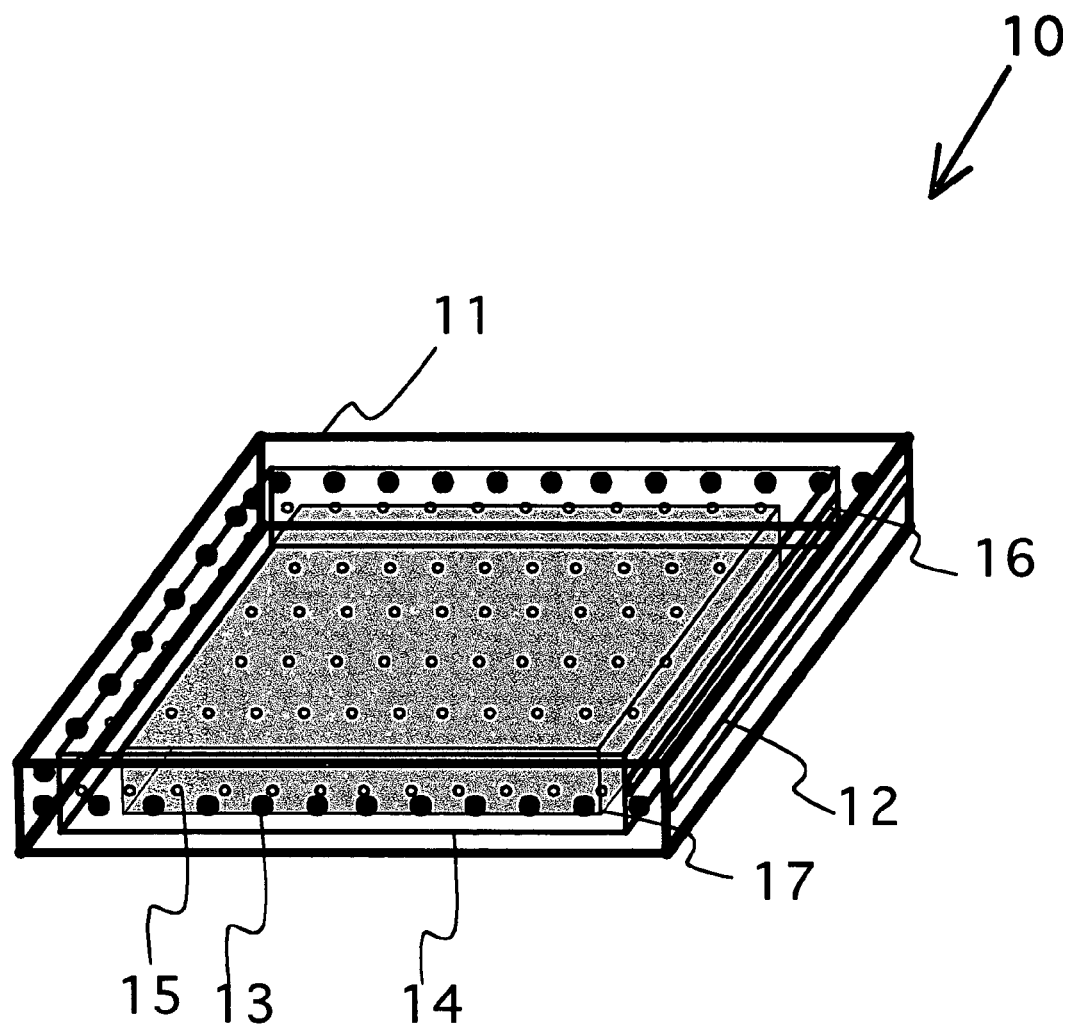
FIG. 1 is a diagrammatic representation of a scent-dispersing mat that incorporates the elements of the present invention.

The present invention's scent dispersing mat apparatus releases scent when force is applied to its external surface, such as being stepped on by a user. The scent dispersing mat apparatus also provides a cushioned contact providing a comfortable surface for stepping on.

Generally stated the scent dispersing mat is easy to use and disperses fragrant scent only when the force is applied to the upper surface of the mat, for example by a user stepping on the mat. The mat comprises an outer housing into which an inner pouch is inserted through a resealable side opening. The inner pouch also has a resealable opening through which a fragrant body is inserted. Thus the fragrant body is easily replaced when its fragrance has completely evaporated. The long life of the fragrant body is assured by having the inner pouch maintain fragrance vapor at saturation thereby preventing further volatilization and releasing the saturated vapor into the outer housing and room air only when a user steps on the scent dispersing mat.

The scent dispersing mat apparatus comprises an air filled cavity formed by a flexible polymeric outer housing which has an upper surface, a lower surface and side surfaces. The lower surface is non-porous while the upper and side surfaces are appointed with several small apertures for dispersing the scent when the user steps on the flexible outer housing. Preferably, the apertures are placed only on the side surfaces since the small apertures on the upper surface may clog due to dirt or debris. These apertures may have a diameter ranging from 0.05 mm to 1 mm. The housing has a sealable opening on one of the sides so that an inner pouch containing fragrant body can be inserted. The inserted inner pouch is a polymeric body with a sealable side opening to receive a fragrant body. In the first embodiment, the inner polymeric pouch has several small apertures ranging in diameter from 0.01 mm to 0.4 mm for dispersing the fragrance when force is applied to the outer housing. The same small apertures also serve to bring fresh air into the inner pouch when force is released on the outer housing.

In the second embodiment, the inner pouch has a number of outward opening flaps that open outward towards the interior of the outer housing serving to dispense the fragrance when force is applied to the outer housing and a number of similarly constructed inward opening flaps open in a direction that is away from the interior of the outer housing serving to bring in fresh air into the inner pouch when force on the outer housing is released. The fragrant body comprises a springy sponge-like member soaked with essential oils that provide the scent. The spring quality of the fragrant body is sufficient to provide cushioning effect when the outer housing is stepped on, releases the fragrance that is volatilized in the inner pouch to the interior of the outer housing which is dispersed into the room through the side holes of the outer housing body. When force on the outer housing is released, the spring quality of the fragrant body is sufficient to enlarge the inner pouch volume to its original value thereby aspirating air into the inner pouch.

The essential oils in the fragrant body are chosen so that they have sufficiently high vapor pressure so that the fragrance in the essential oils volatilizes into the interior of the inner pouch until the vapor is fully saturated. At this point, equilibrium is reached between the vapor-saturated air in the inner pouch and the essential oil liquid contained in the spongy fragrant body and the volatilization process stops. This process begins again only when the saturated vapor is discharged by the user stepping on the outer housing and fresh air is brought in into the inner pouch when force on the outer housing is released. The incoming fresh air has a vapor pressure much less than saturation and therefore the essential oil liquid again vaporizes, saturating the air in the inner pouch. In the first embodiment, small holes in the inner pouch serve to dispense the vapor saturated air into the interior of the outer housing and the same holes serve to bring in fresh air into the interior of the inner pouch. In the second embodiment, the outward facing flaps open to disperse the vapor saturated air from the interior of the inner pouch to the outer housing and the inward facing flaps open to bring fresh air into the inner pouch when force on the outer housing is released. The outward facing flaps are closed when inward facing flaps are open. Also, the inward facing flaps are closed when outward facing flaps are open.

In an alternate embodiment, the spongy fragrant body may be inserted between two rigid metallic or polymeric sheets, which are attached to one or more compression springs. In this case, the springs provide the cushioning function and open the inferior of the inner pouch to bring in fresh air into the interior of the inner pouch. The rigid sheets assure that the entire sponge body is squeezed when force is applied to any part of the fragrant body outer surface. In this embodiment, the fragrant body inserted into a pair of spring supported rigid sheets is handled as one unit and is inserted into the inner pouch through the sealable side opening and the inner pouch is inserted into the outer housing through its resealable side opening.

The resealable openings of the inner pouch and the outer housing may be constructed in the form of tongue and groove, which may be zipped or pressed to create a seal.

Referring to FIG. 1, there is shown at 10 a scent-dispersing mat with an outer housing 11, which has a resealable opening at 12. The outer housing has a number of small apertures 13 for dispersing the scent. An inner pouch 14 is placed within the interior of the outer housing and it has small apertures 15 for dispersing saturated vapor of scent from the interior of the inner pouch to the interior of the outer housing according to the first embodiment for the construction of the inner pouch. The same apertures draw in air into the interior of the inner pouch when force on the outer housing of the scent-dispersing mat is released. The inner pouch also has a resealable opening at 16 for inserting a fragrant body 17 into the interior of the inner pouch. The fragrant body is a springy spongy body that has essential oils having high vapor pressure at ambient temperatures soaked in it so that the essential oils vaporize. The fragrant body contained within the sealed inner pouch vaporizes the essential oils and saturated vapor occupies the entire inner volume of the inner pouch thereby preventing further vaporization. When force is exerted on the outer housing, such as a user stepping on the scent dispersing mat, the inner pouch is squeezed and the saturated vapor is driven through the apertures at 15, mixes with the air in the interior of the outer housing and is released to room air through apertures 13 in the outer housing. When the force on the outer housing is released, the springy fragrant body returns to its original shape, thereby expanding the inner volume of the inner pouch and make up air is drawn through the apertures at 15. Since the volume of inner pouch is now occupied by air that has less than saturation value of fragrant vapor, the essential oil volatilizes to bring the interior volume of the inner pouch to vapor saturation level.

Figure 2:
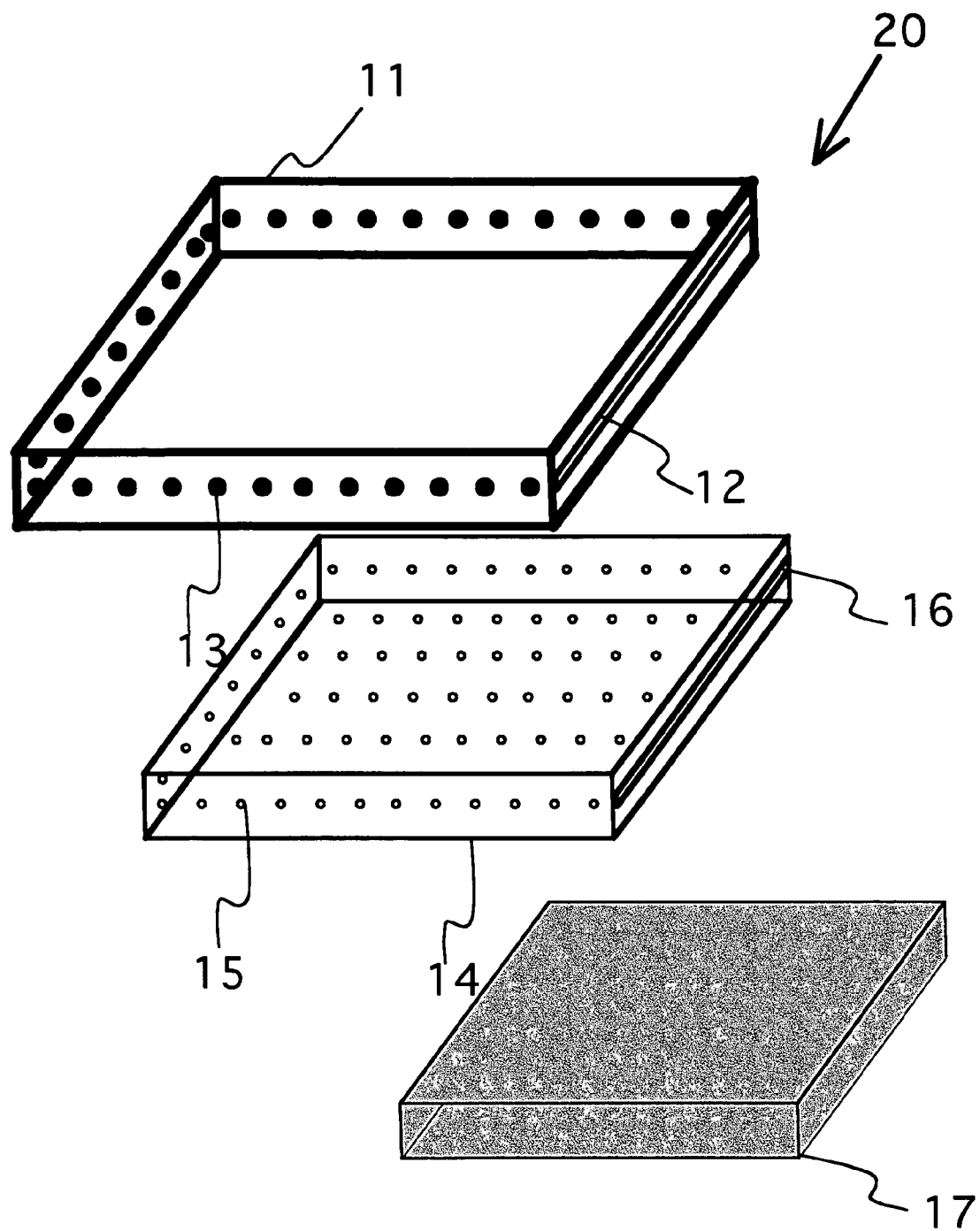
FIG. 2 is a diagrammatic representation of the scent-dispersing mat shown in FIG. 1, illustrating the individual components thereof.

Referring to FIG. 2, there is shown at 20 an exploded view of the individual components of the scent-dispersing mat. The outer housing 11, which has a resealable opening at 12, and a number of small apertures 13 for dispersing the scent is shown. The inner pouch 14, shown as a separate item, has small apertures 15 for dispersing saturated vapor and the resealable opening at 16 for inserting a fragrant body. The fragrant body is shown as a separate item at 17

Figure 3:
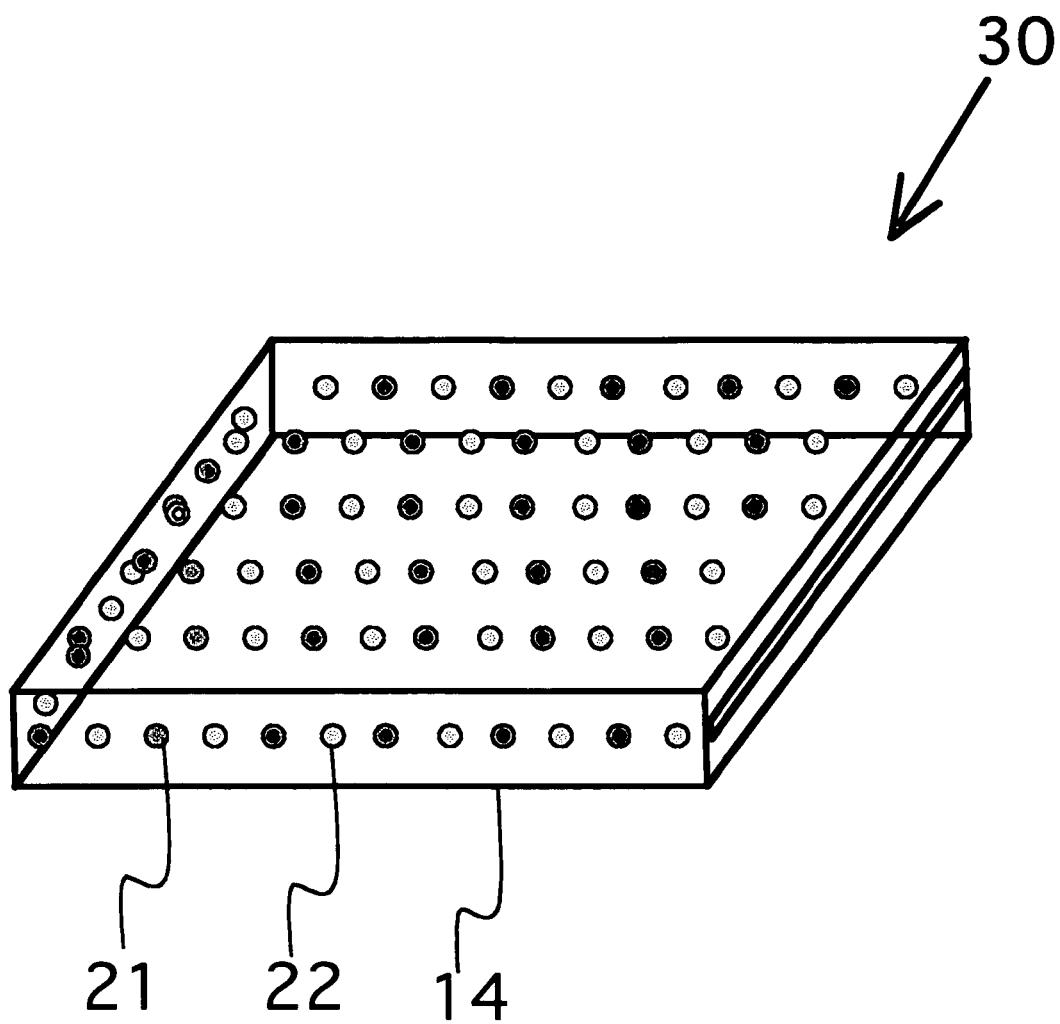
FIG. 3 is a diagrammatic representation of a second embodiment of the scent dispersing mat's inner pouch.

Referring to FIG. 3, a second embodiment is shown at 30 illustrating the alternative construction of the inner pouch. The inner pouch 14 has outward opening flaps 21 which open out when the inner pouch is squeezed. As the flaps 21 open out the saturated vapor contained within the volume of the inner pouch is driven into the interior of the outer housing, when the inner pouch is placed within the outer housing, as detailed in FIG. 1. When the squeezing force is released, the fragrant body contained within the inner pouch pushes against the interior walls of the inner pouch, requiring make-up air to be drawn in. This drawing-in action closes these outward opening flaps 21 and in turn closes and opens inward opening flaps 22. Once air pressures are equilibrated both inward opening flaps 22 and outward opening flaps 21 close creating an enclosed containment for creating saturated vapor within the interior of the inner pouch.

Figure 4:
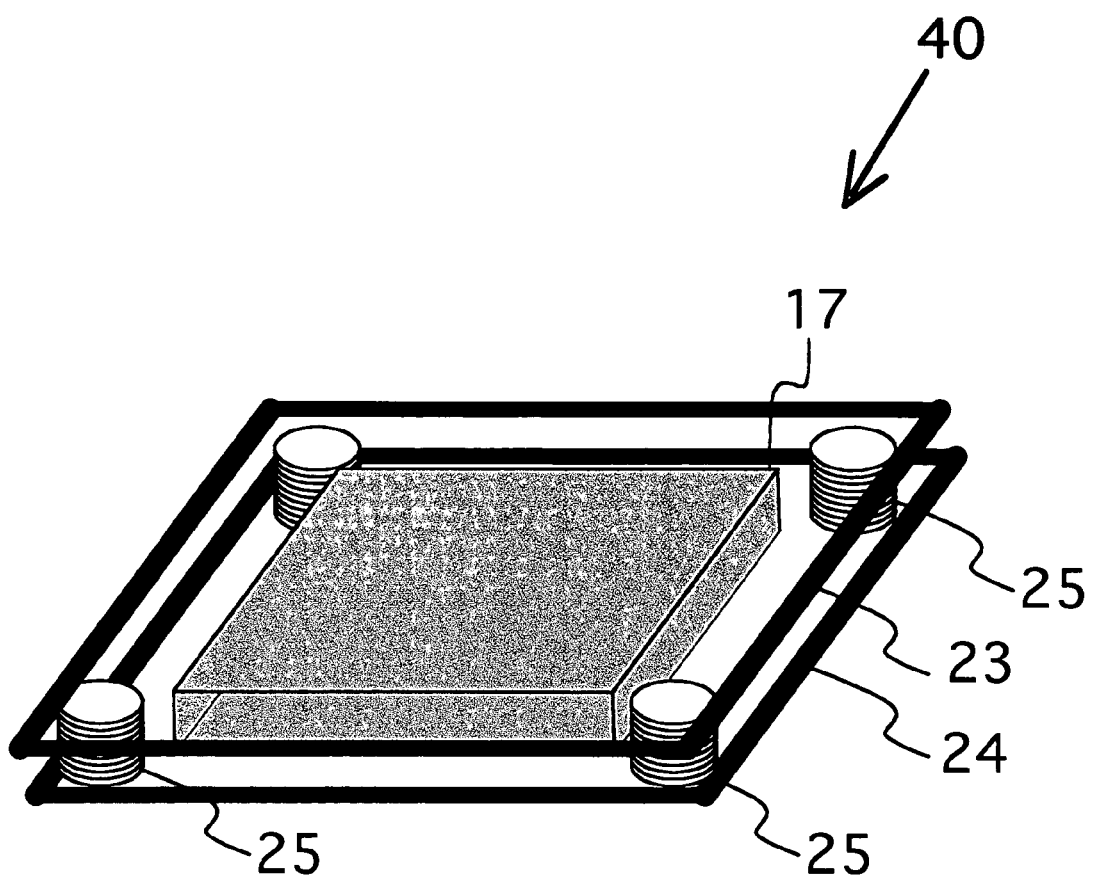
FIG. 4 is a diagrammatic representation of an alternate embodiment of the scent dispersing mat's fragrant body, appointed for insertion into an inner pouch having two spring supported rigid sheets.

Referring to FIG. 4, the fragrant body assembly 40 is shown. Fragrant body 17 is placed between rigid sheets 23 and 24 which are held together by compression springs 25. When force is applied to the outer housing, the inner pouch is squeezed thereby squeezing the fragrant body assembly 40 and releasing saturated vapor from the interior of the inner pouch. When the applied force is removed, the compression springs 25 readjust the interior surface of the inner pouch, thereby drawing fresh make-up air into the interior of the inner pouch.

The key features of the scent-dispersing mat include, in combination, the features set forth below:

1. a flexible outer housing with apertures for dispersing scent from a fragrance body contained therewithin when subjected to force;
2. the flexible outer housing having a resealable opening to insert an inner pouch containing a fragrant body;
3. the inner pouch having small apertures to deliver saturated fragrance vapor contained within its interior to the interior of outer housing when force is applied to outer housing;
4. the inner pouch housing having a resealable opening to insert a fragrant body;
5. a fragrant body spring action bringing inner pouch to its original shape after squeezing thereby drawing make up fresh air into the interior of the inner pouch;
6. the fragrant body comprising a springy spongy polymeric material soaked in essential oils;
7. optionally, the fragrant body being held between two rigid sheets attached to each other by compression springs and inserted as a fragrant body assembly into the inner pouch, the compression springs recovering the shape of the inner pouch after application of force, thereby drawing make up fresh air into the interior of the inner pouch;
8. the essential oils having a high fragrance vapor pressure at ambient temperature thereby volatilizing the essential oil to produce saturated fragrance vapor within the inner pouch;
9. the volume of air within the inner pouch being brought to saturation of fragrance vapor after make up air draw by volatilization of essential oil; and
10. the fragrant body being replaced easily by opening the resealable opening of the outer housing and inner pouch after the essential oils have been exhausted by evaporation.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A scent dispersing mat, comprising;
    a. a flexible outer housing having an upper surface, lower surface and side surfaces, said flexible outer housing comprising an outer surface of said mat, said outer surface having apertures adapted for dispersing a scent;
    b. said flexible outer housing having an interior and a first resealable opening;
    c. an inner pouch contained within said flexible outer housing, having been inserted therein through said first resealable opening, said inner pouch having an inner interior and a plurality of small apertures adapted for dispersing saturated vapor from said inner interior of said inner pouch to said interior of said flexible outer housing;
    d. said inner pouch having a second resealable opening;
    e. a fragrance body contained within said inner pouch, having been inserted therein through said second resealable opening, and comprising a springy spongy rubber or polyurethane polymeric material soaked in essential oils to form a fragrance body sponge spring, said fragrance body sponge spring being in a compressed configuration when a force is applied to said mat and being in a relaxed configuration when said force is not applied to said mat;

f. said essential oils having a high vapor pressure at ambient temperature to volatilize said essential oils adapted to form a saturated fragrance vapor within said inner pouch; and g. said flexible outer housing adapted for releasing said saturated fragrance vapor within said inner pouch into a room when said force is applied to said outer surface of said mat, said room having fresh make-up air therein;

whereby exertion of force on said mat squeezes said inner pouch releasing said saturated fragrance vapor into said interior of said outer housing and out through said apertures in said outer housing and into said room, said exertion of force causing said compressed configuration of said fragrance body sponge spring and releasing said force on said mat operates to draw said fresh make-up air from said room into said inner pouch through said small apertures in said inner pouch upon said relaxed configuration of said fragrance body sponge spring.

2. A scent dispersing mat as recited by claim 1, wherein said flexible outer housing is composed of a rubber, polyvinylchloride, polyethylene, or polypropylene polymeric material.

3. A scent dispersing mat as recited by claim 1, wherein said outer surface's said apertures are located on said upper and said side surfaces of said outer housing.

4. A scent dispersing mat as recited by claim 1, wherein said outer surface's said apertures are located on said side surfaces of said outer housing.

5. A scent dispersing mat as recited by claim 1, wherein said outer surface's said apertures range in size from 0.05 mm to 1 mm.

6. A scent dispersing mat as recited by claim 1, wherein said inner pouch's small apertures have outward opening flaps adapted for releasing said saturated vapor and inward opening flaps adapted for drawing said make-up air into said inner interior of said inner pouch.

7. A scent dispersing mat as recited by claim 1, wherein said inner pouch's small apertures range in size from 0.01 mm to 0.4 mm.

8. A scent dispersing mat as recited by claim 1, wherein said fragrance body is composed of a springy spongy rubber or polyurethane polymeric material.

9. A scent dispersing mat as recited by claim 1, wherein said resealable openings in said outer housing and inner pouch comprise a tongue and groove pressed or zipped closure.

10. A scent dispersing mat as recited by claim 1, wherein said fragrance body is replaced when said essential oils have been exhausted by evaporation.

11. A scent dispersing mat, comprising;

a. a flexible outer housing having an upper surface, lower surface and side surfaces said flexible outer housing comprising an outer surface of said mat, said outer surface having apertures for dispersing scent;

b. said flexible outer housing having an interior and a first resealable opening;

c. an inner pouch contained within said flexible outer housing, having been inserted therein through said first resealable opening, said inner pouch having an inner interior and a plurality of small apertures adapted for dispersing saturated vapor from said inner interior of said inner pouch to said interior of said flexible outer housing;

d. said inner pouch having a second resealable opening;

e. a fragrance body contained within said inner pouch, having been inserted therein through said second resealable opening, and comprising a springy spongy rubber or polyurethane polymeric material soaked in essential oils to form a fragrance body sponge, and held between two rigid steel or polymeric sheets attached to each other by compression springs, said compression springs and said fragrance body sponge being in a compressed configuration when a force is applied to said mat and being in a relaxed configuration when said force is not applied to said mat;

f. said essential oils having high vapor pressure at ambient temperature to volatilize said essential oils forming saturated fragrance vapor within said inner pouch; and g. said flexible outer housing adapted for releasing said saturated fragrance vapor within said inner pouch into a room when said force is applied to said mat, said room having fresh make-up air therein;

whereby exertion of force on said mat squeezes said inner pouch and releases said saturated fragrance vapor into said interior of said outer housing and out through said apertures in said outer housing and into said room said exertion of force causing said compressed configuration of said compression springs and said fragrance body sponge, and releasing said force on said mat operates to draw said fresh make-up air from said room into said inner pouch through said small apertures in said inner pouch causing said relaxed configuration of said compression springs and said fragrance body.

12. A scent dispersing mat as recited by claim 11, wherein said flexible outer housing is composed of a rubber, polyvinylchloride, polyethylene, or polypropylene polymeric material.

13. A scent dispersing mat as recited by claim 11, wherein said outer surface's said apertures are located on said upper and said side surfaces of said outer housing.

14. A scent dispersing mat as recited by claim 11, wherein said outer surface's said apertures are located on said side surfaces of said outer housing.

15. A scent dispersing mat as recited by claim 11, wherein said outer surface's said apertures range in size from 0.05 mm to 1 mm.

16. A scent dispersing mat as recited by claim 11, wherein said inner pouch's said small apertures have outward opening flaps operable for releasing said saturated vapor and inward opening flaps operable for drawing said make up air into said inner interior of said inner pouch.

17. A scent dispersing mat as recited by claim 11, wherein said inner pouch's said small apertures range in size from 0.01 mm to 0.4 mm.

18. A scent dispersing mat as recited by claim 11, wherein said fragrance body is composed of a springy spongy rubber or polyurethane polymeric sponge.

19. A scent dispersing mat as recited by claim 11, wherein said resealable openings in said outer housing and said inner pouch are a tongue and groove pressed or zipped closure.

20. A scent dispersing mat as recited by claim 11, wherein said fragrance body is replaced when said essential oils have been exhausted by evaporation.

* * * * *